US010239914B2

(12) United States Patent
Collins

(10) Patent No.: US 10,239,914 B2
(45) Date of Patent: Mar. 26, 2019

(54) IN-SITU SOLVENT RECYCLING PROCESS FOR SOLID PHASE PEPTIDE SYNTHESIS AT ELEVATED TEMPERATURES

(71) Applicant: CEM Corporation, Matthews, NC (US)

(72) Inventor: Jonathan M. Collins, Charlotte, NC (US)

(73) Assignee: CEM Corporation, Matthews, NC (US)

( * ) Notice: Subject to any disclaimer, the term of this patent is extended or adjusted under 35 U.S.C. 154(b) by 0 days.

(21) Appl. No.: 15/490,090

(22) Filed: Apr. 18, 2017

(65) Prior Publication Data

US 2017/0369524 A1 Dec. 28, 2017

Related U.S. Application Data

(63) Continuation-in-part of application No. 15/299,931, filed on Oct. 21, 2016.

(60) Provisional application No. 62/245,484, filed on Oct. 23, 2015, provisional application No. 62/383,397, filed on Sep. 3, 2016.

(30) Foreign Application Priority Data

Oct. 21, 2016 (WO) ................ PCT/US2016/058181

(51) Int. Cl.
 *C07K 1/04* (2006.01)

(52) U.S. Cl.
 CPC ............. *C07K 1/04* (2013.01); *C07K 1/045* (2013.01)

(58) Field of Classification Search
 CPC ...... B01J 4/00; B01J 19/126; B01J 2204/005; B01J 2208/00; C07K 1/04; C07K 1/045
 See application file for complete search history.

(56) References Cited

U.S. PATENT DOCUMENTS

| 6,288,379 | B1 | 9/2001 | Greene |
| 7,393,920 | B2 | 7/2008 | Collins |
| 7,803,351 | B2 * | 9/2010 | Sharma ............. A61K 49/0002 424/1.11 |

(Continued)

FOREIGN PATENT DOCUMENTS

| WO | WO-2014033297 A1 * | 3/2014 | .......... B01F 11/0002 |
| WO | 2015028599 | 3/2015 | |
| WO | 2017070512 | 4/2017 | |

OTHER PUBLICATIONS

J. Collins, K. Porter, S. Singh and G. Vanier, "High-Efficiency Solid Phase Peptide Synthesis (HE-SPPS)," Org. Lett., vol. 16, pp. 940-943, 2014.

(Continued)

*Primary Examiner* — Jeffrey E. Russel
(74) *Attorney, Agent, or Firm* — Philip Summa; Rebecca Harasimowicz

(57) ABSTRACT

An improvement of deprotection in solid phase peptide synthesis is disclosed. The method includes the steps of adding the deprotection composition in high concentration and small volume to the mixture of the coupling solution, the growing peptide chain, and any excess activated amino acid from the preceding coupling cycle; and without any draining step between the coupling step of the previous cycle and the addition of the deprotection composition for the successive cycle; and with the coupling solution at a temperature of at least 30° C.

6 Claims, 1 Drawing Sheet
Specification includes a Sequence Listing.

In-Situ Solvent Recycling Process for Solid Phase Peptide Synthesis

(56) References Cited

U.S. PATENT DOCUMENTS

| | | |
|---|---|---|
| 2004/0238794 A1 | 12/2004 | Karandikar |
| 2007/0270573 A1 | 11/2007 | Collins |
| 2012/0041173 A1 | 2/2012 | Collins |
| 2013/0034547 A1* | 2/2013 | Kelly .................. C07K 1/1077 424/133.1 |
| 2014/0275481 A1 | 9/2014 | Simon |
| 2017/0226152 A1 | 8/2017 | Collins |

OTHER PUBLICATIONS

M. Beyermann, P. Henklein, A. Klose, R. Sohr and M. Bienert, "Effect of tertiary amine on the carbodiimide-mediated peptide synthesis," Int. J. Peptide Protein Res., vol. 37, pp. 252-256, 1991.

L. Carpino, El-Faham and A., "The Diisopropylcarbodiimide/1-Hydroxy-7-azabenzotriazole System: Segment Coupling and Stepwise Peptide Assembly," Tetrahedron, vol. 55, pp. 6813-6830, 1999.

E. Atherton, N. L Benoiton, E. Brown, R. Sheppard and B. J. Williams, "Racemization of Activaterd, Urethane-protected Aminoacids by p-Dimethylaminopyridine. Significance in Solid-phase Peptide Synthesis," J.C.S. Chem. Comm., pp. 336-337, 1981.

S. Wang, J. Tam, B. Wang and R. Merrifield, "Enhancement of peptide coupling reactions by 4-dimethylaminopyridine," Int. J. Peptide Protein Res., vol. 18, pp. 459-467, 1981.

M. Pennington, "Procedures to Improve Difficult Couplings," in Peptide Synthesis Protocols, Vols. Methods in Molecular Biology—vol. 35, Totowa, NJ, Humana Press, 1995, p. 10.

X. Shangjie, I. Held, B. Kempf, H. Mayr, W. Steglich and H. Zipse, "The DMAP-Catalyzed Acetylation of Alcohols—A Mechanistic Study," Chemistry, vol. 11, pp. 4751-4757, 2005.

P. White, J. Collins and Z. Cox, "Comparative study of conventional and microwave assisted synthesis," in 19th American Peptide Symposium, San Diego, CA, 2005.

A. Tofteng, S. Pedersen, D. Staerk and K. Jensen, "Effect of Residual Water and Microwave Heating on the Half-Life of the Reagents and Reactive Intermediates in Peptide Synthesis," Chemistry, vol. 18, pp. 9024-9031, 2012.

K. Wehrstedt, P. Wandrey and D. Heitkamp, "Explosive properties of 1-hydroxybenzotriazoles," J. Hazard Mater, vol. 126, pp. 1-7, 2005.

M. Itoh, "Peptides. IV. Racemization Suppression by the Use of Ethyl-2-Hydroximino-2- cyanoacetate and Its Amide," Bull. Chem. Soc. Jpn., vol. 46, pp. 2219-2221, 1973.

J. Perich, N. Ede, S. Eagle and a Bray, "Synthesis of phosphopeptides by the Multipin method: Evaluation of coupling methods for the incorporation of Fmoc-Tyr(PO3Bzl,H)-OH, Fmoc- Ser(PO3Bzl,H)-OH and Fmoc-Thr(PO3Bzl,H)-OH," Lett. Pept. Sci., vol. 6, pp. 91-97, 1999.

L. Carpino and A. El-Faham, "Effect of Teriary Bases on O-Benzotriazolyuronium Salt-Induced Peptide Segment coupling;" J. Org. Chem., vol. 59, pp. 695-698, 1994.

T. Lescrinier, R. Busson, H. Winter, C. Hendrix, G. Janssen, C. Pannecouque, J. Rozenski, A. Aerschot and P. Herdewijn, "a-Amino acids derived from ornithine as building blocks for peptide synthesis," J. Pept. Res., vol. 49, pp. 183-189, 1997.

S. Nozaki, "Delay of coupling caused by excess additives," J. Pept. Sci., vol. 12, pp. 147-153, 2006.

R. Subirós-Funosas, R. Prohens, R. Barbas, A. El-Faham and F. Albericio, "Oxyma: An Efficient Additive for Peptide Synthesis to Replace the Benzotriazole-Based HOBt and HOAt with a Lower Risk of Explosion," Chemistry, vol. 15, pp. 9394-9403, 2009.

M. Cezari and L. Juliano, "Studies on lactam formation during coupling procedures of N alpha-N omega-protected arginine derivatives," J. Pept. Res., vol. 9, pp. 88-91, 1996.

Sampson, JH et al. An epidermal growth factor receptor variant III-targeted vaccine is safe and immunogenic in patients with glioblastoma multiforme. Mol. Cancer Ther. 2009; 8: 2773-2779.

Li G, Siddhartha M, Wong AJ. The epidermal growth factor variant III peptide vaccine for treatment of malignant gliomas. Neurosurg. Clin. N. Am. 2010; 21: 87-93.

Li G, Wong AJ. EGF receptor variant III as a target antigen for tumor immunotherapy. Expert Rev. Vaccines 2008; 7:977-985.

R. B. B Merrifield; Solid Phase Peptide Synthesis. I. The Synthesis of a Tetrapeptide; J. Am. Chem. Soc., 1963, 85(14), pp. 2149-2154.

Chan and White, Fmoc Solid Phase Peptide Synthesis, Oxford University Press 2000, p. 1.

Collins, Microwave-enhanced solid-phase peptide synthesis. ChemInform, 39(46) i. 2008.

Bacsa et al., Rapid solid-phase peptide synthesis using thermal and controleld microwave irradiation; Journal Peptide Science, 2006, 12(10), 633-638.

Amblard et al., Methods and protocols of modern solid phase peptide synthesis, Molecular Biotechnology, 2006, 239-254.

Coin et al., Solid-phase peptide synthesis: from standard procedures to the synthesis of difficult sequences; Nature Protocols, 2007, 2(12), 3247-3256.

International Search Report of counterpart Application No. PCT/US2016/058181 dated Jan. 31, 2017.

Finneman et al., "Novel approach for optimization of a 'difficult' peptide synthesis by utilizing quantitative reaction monitoring assays," J. Pept. Sci., 2012; 18: 511-518.

CEM Corporation, Microwave Synthesis of 'difficult' peptide EGFRvIII; 2013; 3 pages.

I. Friligou, E. Papadimitriou, D. Gatos, J. Matsoukas and T. Tselios, "Microwave-assisted solid-phase peptide synthesis of the 60-110 domain of human pleiotrophin on 2-chlorotrityl resin," Amino Acids, vol. 40, pp. 1431-1440, 2011.

R Subirós-Funosas, "Use of Oxyma as pH modulatory agent to be used in the prevention of base-driven side reactions and its effect on 2-chlorotrityl chloride resin," Pept. Sci., vol. 98, pp. 89-97, 2012.

International Search Report of counterpart Application No. PCT/US2017/028254 dated Aug. 1, 2017.

Palasek, et al., Limiting racemization and aspartimide formation on microwave-enhanced Fmoc solid phase peptide synthesis; J. Pept. Sci., 2006; 13: 143-148.

J. Collins, "Microwave-Enhanced Synthesis of Peptides, Proteins, and Peptidomimetics," in Microwaves in Organic Synthesis' 3rd Ed., Weinheim, Germany, Wiley-VCH Verlag & Co KGaA, 2013, pp. 897-960.

Counterpart International Patent Application No. PCT/US2017/028254 filed Apr. 19, 2017 for "In-situ Solvent Recycling Process for Solid Phase Peptide Synthesis at Elevated Temperatures".

Methods for determining enantiomeric purity of amino acids; accessed Oct. 4, 2017 at http://cat-online.com/enantiomeric%20purity.html.

* cited by examiner

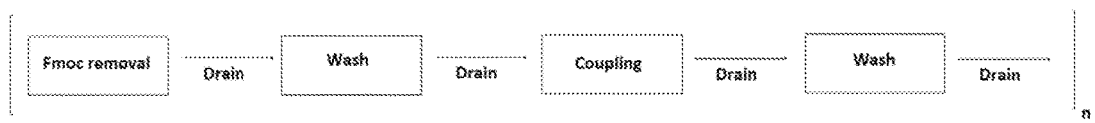
Figure 1—Prior Art: Traditional SPPS Cycle
Figure 2— Prior Art—More recent SPPS Cycles: High Efficiency Solid Phase Peptide Synthesis (HE-SPPS)
Figure 3 In-Situ Solvent Recycling Process for Solid Phase Peptide Synthesis

IN-SITU SOLVENT RECYCLING PROCESS FOR SOLID PHASE PEPTIDE SYNTHESIS AT ELEVATED TEMPERATURES

RELATED APPLICATIONS

This application is a continuation in part of Ser. No. 15/299,931, filed Oct. 21, 2016, for "Improvements in Solid Phase Peptide Synthesis."

This application incorporates by reference the sequence listing submitted on Jun. 19, 2018 in ASCII text file format in accordance with 37 CFR 1.824(a) titled "20180619_amended_sequence_listing" created on Jun. 19, 2018 with a file size of 8 KB. The sequence listing is part of the specification and is herein incorporated by reference in its entirely. In accordance with 37 CFR 1.825(a), the sequence listing contains no new matter.

BACKGROUND

Bruce Merrifield's pioneering development of solid phase peptide synthesis created a useful process for synthesis peptide chains through its use of filtration to remove reagents between steps. The process has involved repetitive cycles which include coupling and deprotection with washing and filtration in-between each step (FIG. 1). It has commonly been assumed that washing is required between each step to completely remove the reagents previously used so that they don't undesirably participate in the next step. This typically involves "insertions" which refer to the incorporation of an extra amino acid. This is thought to occur through either residual base removing the protecting group (Fmoc) on an amino acid recently coupled thereby allowing a second amino acid to "insert"; or through residual activated amino acid left behind during the subsequent deprotection step which could couple to deblocked sites thereby "inserting" an extra amino acid from the previous step. It was recently shown, however, that washing after the coupling step was not required for the successful synthesis of peptides. In this work the coupling step was drained and the deprotection solution was subsequently added to the vessel (J. Collins, K. Porter, S. Singh and G. Vanier, "High-Efficiency Solid Phase Peptide Synthesis (HE-SPPS)," *Org. Lett.*, vol. 16, pp. 940-943, 2014) (FIG. 2).

SUMMARY

The invention is a method of deprotection in solid phase peptide synthesis in which the improvement comprises adding the deprotection composition in high concentration and small volume to the mixture of the coupling solution, the growing peptide chain, and any excess activated amino acid from the preceding coupling cycle; and without any draining step between the coupling step of the previous cycle and the addition of the deprotection composition for the successive cycle; and with the coupling solution at least 30° C.

In another aspect the invention is a method of deprotection in solid phase peptide synthesis in which the improvement comprises adding the deprotection composition in high concentration and small volume to the mixture of the coupling solution, the growing peptide chain, and any excess activated amino acid from the preceding coupling cycle; and without any draining step between the coupling step of the previous cycle and the addition of the deprotection composition for the successive cycle which removes at least 50% of the volume of the previous cycle coupling solution; and with the coupling solution at a temperature of at least 30° C.

The foregoing and other objects and advantages of the invention and the manner in which the same are accomplished will become clearer based on the followed detailed description taken in conjunction with the accompanying drawings.

BRIEF DESCRIPTION OF THE DRAWINGS

FIG. 1 illustrates a traditional SPPS Cycle

FIG. 2 illustrates more recent SPPS Cycles for High Efficiency Solid Phase Peptide Synthesis (HE-SPPS)

FIG. 3 illustrates in-situ solvent recycling process for solid phase peptide synthesis.

DETAILED DESCRIPTION

This invention presents a novel process whereby the coupling and deprotection steps occur within the same solvent. In this process concentrated base is added directly to the resin coupling solution after a desired period of time for the coupling to occur. The deprotection step is then immediately started when the base is added. Therefore, the onset of the deprotection step is immediately after the coupling step without any time delay.

Additionally, only a small volume of base is required since it can use the solvent present from the coupling reaction. This requires a sophisticated reagent delivery system for the base that is accurate at very small volumes (0.5 mL) with rapid delivery. Typically, a 20% solution of base (piperidine) in solvent is used for the deprotection step. Excess base concentration can increase base-catalyzed side reactions and therefore significant solvent is required. This means that significant solvent can be saved from this process by adding concentrated base to the coupling solvent.

To demonstrate the effectiveness of this new process a batch of 24 peptides were assembled using an automated peptide synthesizer modified to perform the in-situ solvent recycling step during each cycle.

Materials and Methods:

All peptides were synthesized using a LIBERTY BLUE™ PRIME™ system (CEM Corp., Matthews, N.C., USA) allowing for automated in-situ solvent recycling and evaporation based washing. The peptides were synthesized at 0.05 mmol scale with 10 equivalents of amino acid using CarboMAX™ coupling with amino acid/carbodiimide/ethyl 2-cyano-2-(hydroxyimino)acetate (AA/DIC/Oxyma) (1:2:1) based activation for 100 sec at 90° C. (E. Atherton, N. L. Benoiton, E. Brown, R. Sheppard and B. J. Williams, "Racemization of Activated, Urethane-protected Aminoacids by p-Dimethylaminopyridine. Significance in Solid Phase Peptide Synthesis," *J.C.S. Chem. Comm.*, pp. 336-337, 1981). ProTide resins (CEM Corp.) based on Tenta-Gel® technology were used for synthesis with either a Rink Amide linker or a Cl-TCP(Cl) linker with unactivated loading of the first amino acid with DIEA at 90° C. for 5 min. The deprotection step was performed for 50 sec at 95° C. and initiated by adding 0.5 mL of 50% pyrrolidine directly to the coupling solution. A single 1×4 mL wash was used in between the deprotection and coupling steps. Peptides were cleaved with Trifluoroacetic acid (TFA)/triisopropylsilane/water/2,2'-(ethylenedioxy)diethanethiol (TFA/TIS/$H_2O$/DODt) (92.5:2.5:2.5:2.5) for 30 min at 38° C. using a RAZOR™ cleavage system (CEM Corp.).

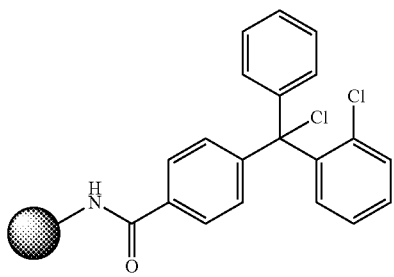

Cl-TCP(Cl)-ProTide

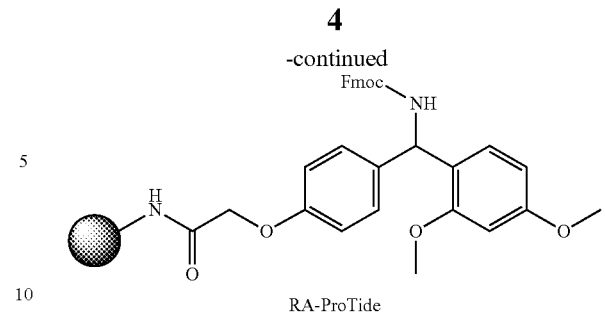

RA-ProTide

Results and discussion:

TABLE 1

Automated Sequential Batch Synthesis of 24 Peptides

| # | Peptide | Disease Area | Resin Used | UPLC Purity | Synthesis Time |
|---|---------|--------------|------------|-------------|----------------|
| 1 | GRP (SEQ ID NO: 1)<br>VPLPAGGGTVLTKMYPRGNHWAVGHLM-NH$_2$ | Regulates Gastrin Release | RA ProTide | 81 | 1:22 |
| 2 | Glucagon (SEQ ID NO: 2)<br>H-HSQGTFTSDYSKYLDSRRAQDFVQWLMNT-NH$_2$ | Hypoglycemia | RA ProTide | 75 | 1:28 |
| 3 | Bivalirudin (SEQ ID NO: 3)<br>H-fPRPGGGGNGDFEEIPEEYL-OH | Blood thinner | Cl-2-Cl-Trt | 71 | 1:05 |
| 4 | Angiotensin (SEQ ID NO: 4)<br>H-NRVYVHPF-OH | Vasoconstrictor | Cl-2-Cl-Trt | 82 | 0:30 |
| 5 | PTH 1-34 (SEQ ID NO: 5)<br>H-SVSEIQLMHNLGKHLNSMERVEWLRKKLQDVHNF-NH$_2$ | Osteoporosis | RA ProTide | 70 | 1:43 |
| 6 | Gonadorelin (SEQ ID NO: 6)<br>pEHWSYGLRPG-NH$_2$ | Fertility | RA ProTide | 91 | 0:35 |
| 7 | Triptorelin (SEQ ID NO: 7)<br>pEHWSYwLRPG-NH$_2$ | Breast Cancer, Prostrate Cancer, | RA ProTide | 73 | 0:35 |
| 8 | Liraglutide (SEQ ID NO: 8)<br>H-HAEGTFTSDVSSYLEGQAAK(γ-E-palmitoyl)EFIAWLVRGRG-NH$_2$ | Diabetes | RA ProTide | 80 | 1:31 |
| 9 | Exenatide (SEQ ID NO: 9)<br>H-HGEGTFTSDLSKQMEEEAVRLFIEWLKNGGPSSGAPPPS-NH$_2$ | Diabetes | RA ProTide | 74 | 1:58 |
| 10 | MOG (35-55) (SEQ ID NO: 10)<br>H-MEVGWYRSPFSRVVHLYRNGK-NH$_2$ | Multiple Sclerosis | RA ProTide | 71 | 1:05 |
| 11 | Secretin (SEQ ID NO: 11)<br>H-HDGTFTSELSRLRDSARLQRLLQGLV-NH$_2$ | Osmoregulation | RA ProTide | 70 | 1:19 |
| 12 | Teriparatide (SEQ ID NO: 12)<br>H-SVSEIQLMHNLGKHLNSMERVEWLRKKLQDVHNF-NH$_2$ | Osteoporosis | RA ProTide | 60 | 1:43 |
| 13 | GLP-1 (7-37) (SEQ ID NO: 13)<br>H-HAEGTFTSDVSSYLEGQAAKEFIAWLVKGRG-NH$_2$ | Diabetes | RA ProTide | 74 | 1:34 |
| 14 | Magainin 1 (SEQ ID NO: 14)<br>H-GIGKFLHSAGKFGKAFVGEIMKS-NH$_2$ | Antibiotic | RA ProTide | 79 | 1:11 |
| 15 | Tetracosactide (SEQ ID NO: 15)<br>H-SYSMEHFRWGKPVGKKRRPVKVYP-NH$_2$ | Adrenal Cortex stimulant | RA ProTide | 77 | 1:13 |
| 16 | [Arg8]-Vasopressin (SEQ ID NO: 16)<br>H-CYFQNCPRG-NH$_2$ | Hormone (blood vessel | RA ProTide | 94 | 0:32 |
| 17 | Ubiquitin (SEQ ID NO: 17)<br>MQIFVKTLTGKTITLEVEPSDTIENVKAKIQDKEGIPPDQ<br>QRLIFAGKQLEDGRTLSDYNIQKESTLHLVLRLRGG-NH$_2$ | Protein signaling agent | RA ProTide | ≥60 | 3:44 |

TABLE 1-continued

Automated Sequential Batch Synthesis of 24 Peptides

| # | Peptide | Disease Area | Resin Used | UPLC Purity | Synthesis Time |
|---|---------|--------------|------------|-------------|----------------|
| 18 | Parasin I (SEQ ID NO: 18)<br>H-KGRGKQGGKVRAKAKTRSS-NH$_2$ | Antibiotic | RA ProTide | 87 | 0:59 |
| 19 | Dynorphin A (SEQ ID NO: 19)<br>H-YGGFLRRIRPKLKWDNQ-NH$_2$ | Opioid Research | RA ProTide | 71 | 0:53 |
| 20 | ACP (SEQ ID NO: 20)<br>H-VQAAIDYING-NH$_2$ | Fatty Acid Synthesis | RA ProTide | 92 | 0:32 |
| 21 | BAM 3200 (SEQ ID NO: 21)<br>H-YGGFMRRVGRPEWWMDYQKRYGGFL-NH$_2$ | Opioid Research | RA ProTide | 70 | 1:16 |
| 22 | HIV-TAT (47-57) (SEQ ID NO: 22)<br>Fmoc-YGRKKRRQRRR-NH$_2$ | HIV/AIDS Research | RA ProTide | 93 | 0:31 |
| 23 | HIV-TAT (48-60) (SEQ ID NO: 23)<br>Fmoc-GRKKRRQRRRPPQ-NH$_2$ | HIV/AIDS Research | RA ProTide | 88 | 0:39 |
| 24 | Pramlintide (SEQ ID NO: 24)<br>KCNTATCATQRLANFLVHSSNNFGPILPPTNVGSNTY--NH$_2$ | Diabetes | RA ProTide | 72 | 1:52 |

All peptides synthesized in Table 1 gave the desired target as the major peak with a standard cycle time of 2 minutes and 58 seconds. The in-situ solvent recycling process allowed for 0.5 mL of a concentrated pyrrolidine (BP 87° C.) solution to be added to the end of the coupling step (without draining). An advantage of this setup was that the deprotection immediately proceeded very close to the desired temperature (95° C.) because the coupling solution was already at 90° C. During the deprotection process a vacuum was applied and the pyrrolidine was evaporated and subsequently condensed in the waste container. This allowed only a single wash step (1×4 mL) to be required at the end of the deprotection step.

Total synthesis time for entire batch: 32.6 hours

This new process provided a significant reduction in standard cycle time (2 minutes 57 seconds) from (a)—elimination of the coupling drain time, (b)—elimination of the deprotection delivery time between steps, and (c)—elimination of the temperature ramp time for the deprotection step thereby allowing a shorter deprotection time to be used. Additionally, significant solvent savings were possible with the complete elimination of the deprotection solvent during each cycle.

In the drawings and specification there has been set forth a preferred embodiment of the invention, and although specific terms have been employed, they are used in a generic and descriptive sense only and not for purposes of limitation, the scope of the invention being defined in the claims.

The invention claimed is:

1. A method of deprotection in batch solid phase peptide synthesis in which the improvement comprises:
    adding a base deprotection composition to a mixture of a coupling solution, a growing peptide chain, and any excess activated amino acid from a preceding coupling step;
    wherein the deprotection composition has a concentration of at least 50% base by volume and is added to the mixture of the coupling solution, the growing peptide chain, and any excess activated amino acid from the preceding coupling step in an amount that is less than 1/3 of the volume of the coupling solution;
    without any draining step between the coupling step of the preceding coupling cycle and the addition of the deprotection composition for the successive cycle; and
    with the coupling solution at least 30° C.

2. A method according to claim 1 wherein the deprotection composition is an organic base.

3. A method according to claim 1 using Fmoc solid phase peptide chemistry.

4. A method of deprotection in batch solid phase peptide synthesis in which the improvement comprises:
    adding a base deprotection composition to a mixture of a coupling solution, a growing peptide chain, and any excess activated amino acid from the preceding coupling cycle step;
    wherein the deprotection composition is added to the mixture of the coupling solution, the growing peptide chain, and any excess activated amino acid from the preceding coupling step in a concentration of at least 50% base by volume and an amount that is less than 1/3 of the volume of the coupling solution;
    without any draining step between the coupling step of the preceding coupling cycle and the addition of the deprotection composition for the successive cycle which removes at least 50% of the volume of the preceding coupling cycle coupling solution; and
    with the coupling solution at a temperature of at least 30° C.

5. A method according to claim 4 wherein the deprotection composition is an organic base.

6. A method according to claim 4 using Fmoc solid phase peptide chemistry.

* * * * *

SEQUENCE LISTING

```
<160> NUMBER OF SEQ ID NOS: 24

<210> SEQ ID NO 1
<211> LENGTH: 27
<212> TYPE: PRT
<213> ORGANISM: Artificial Sequence
<220> FEATURE:
<223> OTHER INFORMATION: Synthesized

<400> SEQUENCE: 1

Val Pro Leu Pro Ala Gly Gly Gly Thr Val Leu Thr Lys Met Tyr Pro
1               5                   10                  15

Arg Gly Asn His Trp Ala Val Gly His Leu Met
            20                  25

<210> SEQ ID NO 2
<211> LENGTH: 29
<212> TYPE: PRT
<213> ORGANISM: Artificial Sequence
<220> FEATURE:
<223> OTHER INFORMATION: Synthesized

<400> SEQUENCE: 2
```

```
His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 3
<211> LENGTH: 20
<212> TYPE: PRT
<213> ORGANISM: Artificial Sequence
<220> FEATURE:
<223> OTHER INFORMATION: Synthesized

<400> SEQUENCE: 3

Phe Pro Arg Pro Gly Gly Gly Asn Gly Asp Phe Glu Glu Ile Pro
1               5                   10                  15

Glu Glu Tyr Leu
            20

<210> SEQ ID NO 4
<211> LENGTH: 8
<212> TYPE: PRT
<213> ORGANISM: Artificial Sequence
<220> FEATURE:
<223> OTHER INFORMATION: Synthesized

<400> SEQUENCE: 4

Asn Arg Val Tyr Val His Pro Phe
1               5

<210> SEQ ID NO 5
<211> LENGTH: 34
<212> TYPE: PRT
<213> ORGANISM: Artificial Sequence
<220> FEATURE:
<223> OTHER INFORMATION: Synthesized

<400> SEQUENCE: 5

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His Asn Phe
            20                  25                  30

<210> SEQ ID NO 6
<211> LENGTH: 10
<212> TYPE: PRT
<213> ORGANISM: Artificial Sequence
<220> FEATURE:
<223> OTHER INFORMATION: Synthesized

<400> SEQUENCE: 6

Glu His Trp Ser Tyr Gly Leu Arg Pro Gly
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthesized

<400> SEQUENCE: 7

Glu His Trp Ser Tyr Trp Leu Arg Pro Gly
1               5                   10
```

<210> SEQ ID NO 8
<211> LENGTH: 31
<212> TYPE: PRT
<213> ORGANISM: Artificial Sequence
<220> FEATURE:
<223> OTHER INFORMATION: Synthesized

<400> SEQUENCE: 8

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 9
<211> LENGTH: 39
<212> TYPE: PRT
<213> ORGANISM: Artificial Sequence
<220> FEATURE:
<223> OTHER INFORMATION: Synthesized

<400> SEQUENCE: 9

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 10
<211> LENGTH: 21
<212> TYPE: PRT
<213> ORGANISM: Artificial Sequence
<220> FEATURE:
<223> OTHER INFORMATION: Synthesized

<400> SEQUENCE: 10

Met Glu Val Gly Trp Tyr Arg Ser Pro Phe Ser Arg Val Val His Leu
1               5                   10                  15

Tyr Arg Asn Gly Lys
            20

<210> SEQ ID NO 11
<211> LENGTH: 26
<212> TYPE: PRT
<213> ORGANISM: Artificial Sequence
<220> FEATURE:
<223> OTHER INFORMATION: Synthesized

<400> SEQUENCE: 11

His Asp Gly Thr Phe Thr Ser Glu Leu Ser Arg Leu Arg Asp Ser Ala
1               5                   10                  15

Arg Leu Gln Arg Leu Leu Gln Gly Leu Val
            20                  25

<210> SEQ ID NO 12
<211> LENGTH: 34
<212> TYPE: PRT
<213> ORGANISM: Artificial Sequence
<220> FEATURE:
<223> OTHER INFORMATION: Synthesized

<400> SEQUENCE: 12

Ser Val Ser Glu Ile Gln Leu Met His Asn Leu Gly Lys His Leu Asn
1               5                   10                  15

```
Ser Met Glu Arg Val Glu Trp Leu Arg Lys Lys Leu Gln Asp Val His
            20                  25                  30

Asn Phe

<210> SEQ ID NO 13
<211> LENGTH: 31
<212> TYPE: PRT
<213> ORGANISM: Artificial Sequence
<220> FEATURE:
<223> OTHER INFORMATION: Synthesized

<400> SEQUENCE: 13

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 14
<211> LENGTH: 23
<212> TYPE: PRT
<213> ORGANISM: Artificial Sequence
<220> FEATURE:
<223> OTHER INFORMATION: Synthesized

<400> SEQUENCE: 14

Gly Ile Gly Lys Phe Leu His Ser Ala Gly Lys Phe Gly Lys Ala Phe
1               5                   10                  15

Val Gly Glu Ile Met Lys Ser
            20

<210> SEQ ID NO 15
<211> LENGTH: 24
<212> TYPE: PRT
<213> ORGANISM: Artificial Sequence
<220> FEATURE:
<223> OTHER INFORMATION: Synthesized

<400> SEQUENCE: 15

Ser Tyr Ser Met Glu His Phe Arg Trp Gly Lys Pro Val Gly Lys Lys
1               5                   10                  15

Arg Arg Pro Val Lys Val Tyr Pro
            20

<210> SEQ ID NO 16
<211> LENGTH: 9
<212> TYPE: PRT
<213> ORGANISM: Artificial Sequence
<220> FEATURE:
<223> OTHER INFORMATION: Synthesized

<400> SEQUENCE: 16

Cys Tyr Phe Gln Asn Cys Pro Arg Gly
1               5

<210> SEQ ID NO 17
<211> LENGTH: 76
<212> TYPE: PRT
<213> ORGANISM: Artificial Sequence
<220> FEATURE:
<223> OTHER INFORMATION: Synthesized

<400> SEQUENCE: 17

Met Gln Ile Phe Val Lys Thr Leu Thr Gly Lys Thr Ile Thr Leu Glu
1               5                   10                  15
```

-continued

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 18
<211> LENGTH: 19
<212> TYPE: PRT
<213> ORGANISM: Artificial Sequence
<220> FEATURE:
<223> OTHER INFORMATION: Synthesized

<400> SEQUENCE: 18

Lys Gly Arg Gly Lys Gln Gly Gly Lys Val Arg Ala Lys Ala Lys Thr
1               5                   10                  15

Arg Ser Ser

<210> SEQ ID NO 19
<211> LENGTH: 17
<212> TYPE: PRT
<213> ORGANISM: Artificial Sequence
<220> FEATURE:
<223> OTHER INFORMATION: Synthesized

<400> SEQUENCE: 19

Tyr Gly Gly Phe Leu Arg Arg Ile Arg Pro Lys Leu Lys Trp Asp Asn
1               5                   10                  15

Gln

<210> SEQ ID NO 20
<211> LENGTH: 10
<212> TYPE: PRT
<213> ORGANISM: Artificial Sequence
<220> FEATURE:
<223> OTHER INFORMATION: Synthesized

<400> SEQUENCE: 20

Val Gln Ala Ala Ile Asp Tyr Ile Asn Gly
1               5                   10

<210> SEQ ID NO 21
<211> LENGTH: 25
<212> TYPE: PRT
<213> ORGANISM: Artificial Sequence
<220> FEATURE:
<223> OTHER INFORMATION: Synthesized

<400> SEQUENCE: 21

Tyr Gly Gly Phe Met Arg Arg Val Gly Arg Pro Glu Trp Trp Met Asp
1               5                   10                  15

Tyr Gln Lys Arg Tyr Gly Gly Phe Leu
            20                  25

<210> SEQ ID NO 22
<211> LENGTH: 11
<212> TYPE: PRT
<213> ORGANISM: Artificial Sequence
<220> FEATURE:
<223> OTHER INFORMATION: Synthesized

```
<400> SEQUENCE: 22

Tyr Gly Arg Lys Lys Arg Arg Gln Arg Arg Arg
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Synthesized

<400> SEQUENCE: 23

Gly Arg Lys Lys Arg Arg Gln Arg Arg Arg Pro Pro Gln
1               5                   10

<210> SEQ ID NO 24
<211> LENGTH: 37
<212> TYPE: PRT
<213> ORGANISM: Artificial Sequence
<220> FEATURE:
<223> OTHER INFORMATION: Synthesized

<400> SEQUENCE: 24

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
                20                  25                  30

Gly Ser Asn Thr Tyr
            35
```